(12) United States Patent
Cofer

(10) Patent No.: US 7,559,125 B2
(45) Date of Patent: Jul. 14, 2009

(54) CLIP HAVING A SHEATH FOR HOLDING TUBING OR CORDS

(76) Inventor: Carol Cofer, 5018 Hanging Moss La., Sarasota, FL (US) 34238

( * ) Notice: Subject to any disclaimer, the term of this patent is extended or adjusted under 35 U.S.C. 154(b) by 264 days.

(21) Appl. No.: 11/516,694

(22) Filed: Sep. 7, 2006

(65) Prior Publication Data

US 2008/0092349 A1    Apr. 24, 2008

(51) Int. Cl.
*A44B 21/00*    (2006.01)
(52) U.S. Cl. .............................. 24/487; 24/499; 24/500
(58) Field of Classification Search .................. 24/488, 24/489, 499, 500, 501, 509, 507, 134 N; 606/157
See application file for complete search history.

(56) References Cited

U.S. PATENT DOCUMENTS

| | | | |
|---|---|---|---|
| 3,521,332 A | 7/1970 | Kramer | |
| 4,096,863 A | 6/1978 | Kaplan et al. | |
| 4,308,642 A | 1/1982 | Heyman | |
| 4,639,980 A | 2/1987 | Peterson | |
| 4,707,906 A | 11/1987 | Posey | |
| 4,763,390 A | 8/1988 | Rooz | |
| 5,037,397 A | 8/1991 | Kalt | |
| 5,163,914 A | 11/1992 | Abel | |
| 5,395,344 A | 3/1995 | Beisang, III et al. | |
| 5,542,209 A | 8/1996 | Sheu | |
| 5,655,270 A | 8/1997 | Boisvert | |
| 5,871,189 A | 2/1999 | Hoftman | |
| 5,884,372 A | 3/1999 | Anscher et al. | |
| 5,979,110 A * | 11/1999 | Tai | 47/41.01 |
| 6,105,218 A | 8/2000 | Reekie | |
| 6,158,095 A * | 12/2000 | Lassiter | 24/339 |
| 6,298,526 B1 | 10/2001 | Baumdicker et al. | |
| 6,523,231 B1 | 2/2003 | Lassiter | |
| 2003/0188403 A1 | 10/2003 | Lemke et al. | |
| 2006/0021203 A1* | 2/2006 | Nails | 24/499 |

* cited by examiner

*Primary Examiner*—Robert J Sandy
(74) *Attorney, Agent, or Firm*—Kramer & Amado, P.C.; Terry W. Kramer

(57) ABSTRACT

A clip for use in holding cords or tubing, comprising an upper jaw and a lower jaw, each of them having a grasping part and articulated with respect to the other about a hinge between a closed position and an open position; a spring biasing the jaws into the closed position; a tubular sheath having a longitudinal opening, connected between the jaws; and a means for moving the jaws into the open position. The longitudinal opening is open when the jaws are in the open position and closed when the jaws are in the closed position. The sheath is adapted to receive cords or tubing through the longitudinal opening when the jaws are in the open position, and retain the cords or tubing when the jaws are in the closed position. The sheath is adapted to retain medical tubing or electrical cords.

27 Claims, 5 Drawing Sheets

CLIP HAVING A SHEATH FOR HOLDING TUBING OR CORDS

BACKGROUND OF THE INVENTION

1. Field of the Invention

This invention relates generally to a clip for holding tubing, particularly medical tubing, or cords, particularly electrical cords.

More particularly, the invention relates to a clip which has jaws which may be opened to receive cords or tubing. The clip has a sheath which retains the cords or tubing, and prevents them from being caught between the jaws.

2. Description of Related Art

During surgical procedures, an anesthesiologist draws away mucus, saliva and other body fluids such as blood by suction from the patient's mouth and nose. The apparatus used for the continuous or intermittent suctioning operation comprises a tube capable of withstanding vacuum for drawing bodily fluids to a catch bottle. Often, the catheter falls to the floor and is unacceptably contaminated and must be replaced immediately, causing unnecessary delay while searching for new tubing and suction tips. Replacement of accidentally contaminated suction tubing can add to the expense of a medical procedure. Additionally, delay while searching for new tubing at a critical point during surgery may place a patient's life and/or health at risk, and increase the potential liability for medical personnel if something goes wrong during surgery.

In addition, a surgical procedure may require that associated suction tubing or electrical cord for electrosurgical instruments must be maintained in a sterile field. The suction tubing or electrical cord are sometimes merely secured under the O.R. mattress by pressure of the patient on the mattress, increasing the likelihood of contamination and cross-infection.

The current invention solves these problems by providing a clip which may be used to secure suction tubing or electrical cord used in a surgical procedure to a tray.

Additionally, the clip of the current invention has significant utility in both pre- and post-operative patient care. There are a number of situations where it is necessary to secure various form of medical tubing to a patient. For example, drainage tubes are used during and after a variety of procedures. For example, lumpectomy (removal of a breast lump) and mastectomy (removal of the breast) are common surgical treatments for breast cancer. After lumpectomy and mastectomy, many surgeons will place a plastic or rubber drainage tube in the breast or under the arm to help remove blood and lymph which accumulates during the healing process. The tubes are normally attached to drainage bulbs, and may be pinned to a hospital gown. Drainage tubes may also be required for other types of procedures.

Intravenous (IV) tubing, used to administer fluids to a patient, poses a similar problem. It is frequently necessary to transport patients having IV tubes from one point in a hospital to another. These patients are commonly transported in a wheelchair, or on a gurney. Occasionally, the IV tubes may be entangled in the spokes or around the axle of the wheelchair or the gurney.

As a patient becomes mobile, it is not uncommon for drainage tubes or I.V. tubes to pull loose from hospital gowns or sheets, or to become entangled around objects. This is most likely to happen as a patient gets in and out of bed, or as he begins to walk after surgery. In a worst-case scenario, a drainage tube which becomes entangled about an object may actually be pulled out of the patient, requiring surgery to replace it. This causes increased risk to the patient, as well as increased liability to the hospital.

The current invention solves these problems by providing a clip which may be used to securely fasten drainage tubes or IV tubing to clothing, or to sheets or bedding, thereby preventing entangling of the tubing.

Some clips in common use have jaws which may accidentally close on the medical tubing, potentially thereby retarding or stopping flow of fluids through the tubing. This can impede administration of fluids to, or drainage of fluids from, a patient. The current invention is designed to prevent the jaws of the clip from closing on medical tubing.

Finally, the clip of the current invention may be used to secure household electrical cords from lamps, audio/video equipment, etc., to fabric surfaces to prevent the cords from passing across high traffic areas in a room, where a person may trip over them. For example, the clip may be used to secure an electrical cord to the skirt of a cloth chair covering, to the edge of an area rug, to a curtain, or to a tablecloth.

It is an object of the invention to provide a clip which may be used to secure suction tubing or electrical cord used in a surgical procedure to a tray.

It is a further object of the invention to provide a clip which may be used to manage pre- or post-operative medical tubing attached to a patient, so as to prevent entanglement of tubing.

In another object of the invention, a clip is provided which may be used to secure medical tubing while protecting the tubing from contact with the jaws of the clip.

In an additional object of the invention, a clip is provided which may be used to manage electrical cords in a home environment.

The foregoing objects and advantages of the invention are illustrative of those that can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variation which may be apparent to those skilled in the art. Accordingly, the present invention resides in the novel methods, arrangements, combinations and improvements herein shown and described.

SUMMARY OF THE INVENTION

In light of the present need for an improved clip for managing medical tubing and/or electrical cords, a brief summary of the present invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

The current invention is a clip for use in holding cords or tubing, comprising an upper jaw and a lower jaw, each of them having a grasping part and articulated with respect to the other about a hinge between a closed position and an open position; and a spring biasing the jaws into the closed position. A tubular sheath having a longitudinal opening is mounted between said jaws, so that the longitudinal opening is open when the jaws are open and closed when the jaws are closed. The sheath is adapted to receive cords or tubing through the longitudinal opening when said jaws are open, and retain said cords or tubing when said jaws are closed. The clip further includes a means for moving the jaws into said open position.

BRIEF DESCRIPTION OF THE DRAWINGS

In order to better understand the present invention, reference is made to the accompanying drawings, wherein.

DETAILED DESCRIPTION OF THE PREFERRED EMBODIMENTS OF THE INVENTION

Figure 1:
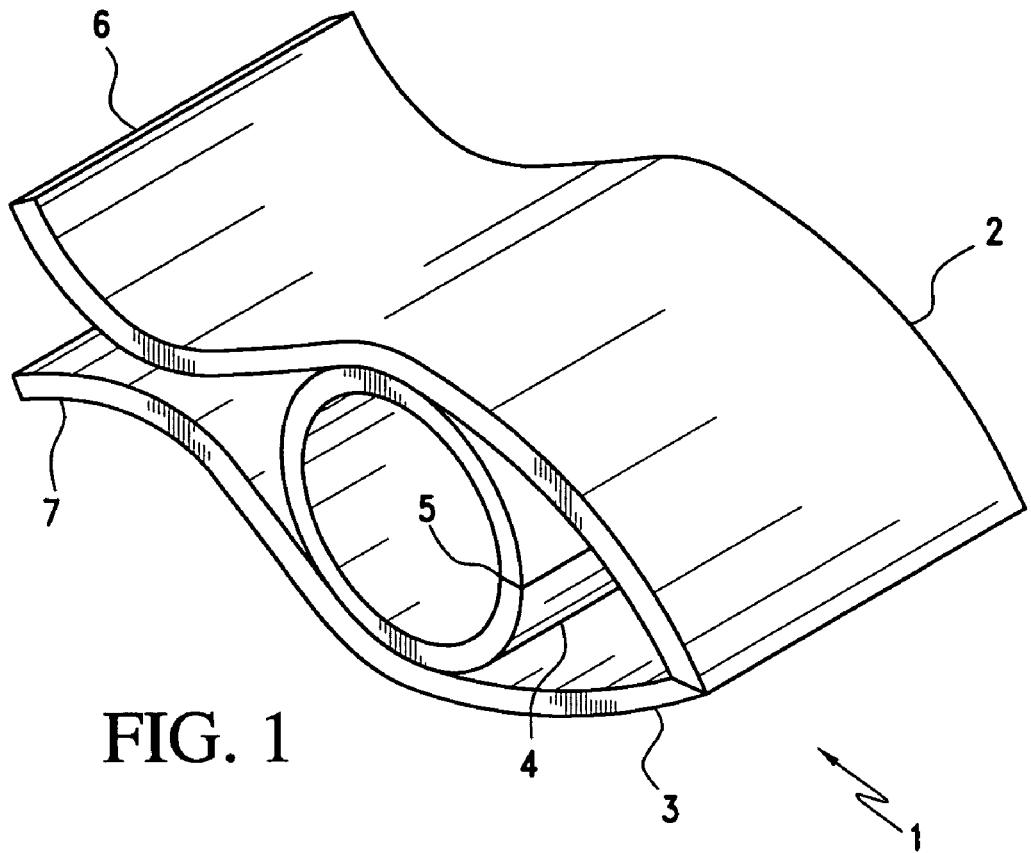
FIG. 1 shows a view of a clip according to the current invention.
Figure 2:
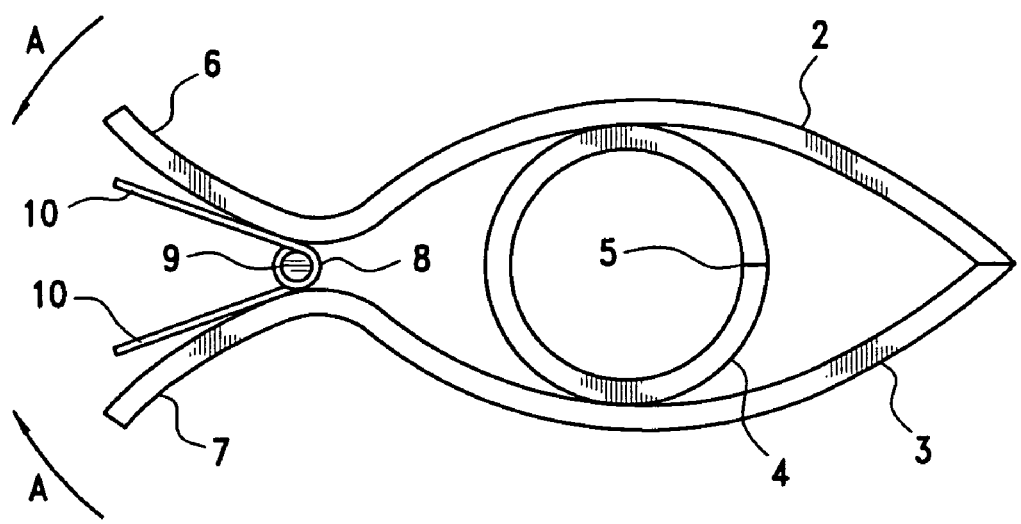
FIG. 2 shows a cross-sectional view of a clip according to FIG. 1, where the clip is in a closed position.
Figure 3:
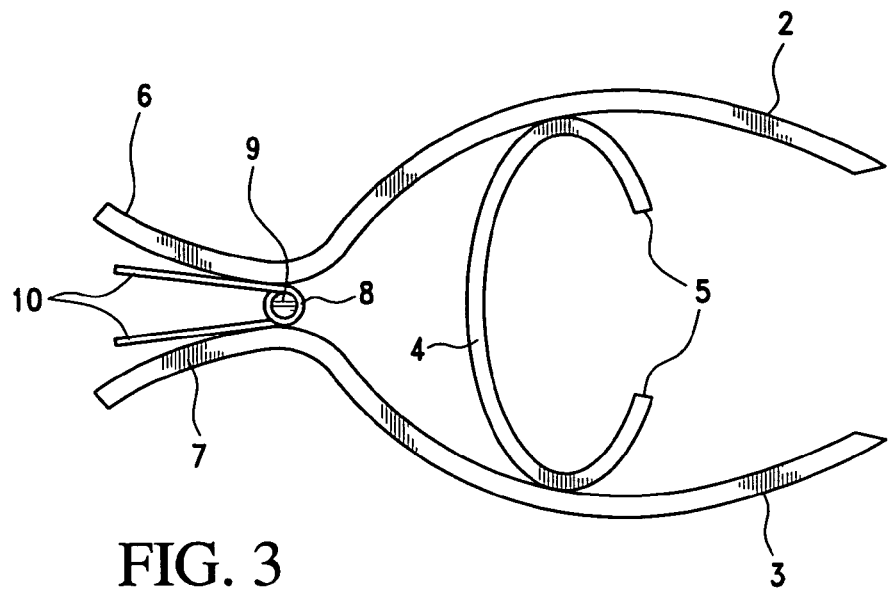
FIG. 3 shows a cross-sectional view of a clip according to FIG. 1, where the clip is in an open position.

Referring now to the drawings, in which like numerals refer to like components or steps, there are disclosed broad aspects of the preferred embodiments of the present invention. FIG. 1 shows a clip 1 according to the current invention. Clip 1 features an upper jaw 2 and a lower jaw 3. Each jaw has a grasping edge; in the embodiment of FIG. 1, these grasping edges are linear. Jaws 2 and 3 are articulated about a hinge (not shown in FIG. 1), allowing them to be moved between a closed position, as seen in FIG. 2, and an open position, as seen in FIG. 3. Mounted in between jaws 2 and 3 is a tubular sheath 4, with a longitudinal slit running through the wall of the sheath. The longitudinal slit is directed toward the grasping edges of jaws 2 and 3. As shown in FIG. 1, the tubular sheath may have a circular cross section; however, this is not required. The tubular sheath may have an oval or polygonal cross section. Upper jaw 2 has a handle 6 and lower jaw 3 has a handle 7. As shown in FIGS. 2 and 3, moving the handles 6 and 7 toward each other in the direction of the arrows causes the clip to open. Helical spring 8, as shown in FIG. 2, is mounted about an axle 9 of the hinge; linear projections 10 at each end of the spring press against handles 6 and 7, causing the jaws of the spring to be biased into a closed position. When the handles are pressed together in the direction of arrows A (FIG. 2), tension is placed on the spring as the jaws open (FIG. 3). Releasing the handles relieves the tension on the spring, and the spring urges the jaws into a closed position.

Figure 4:
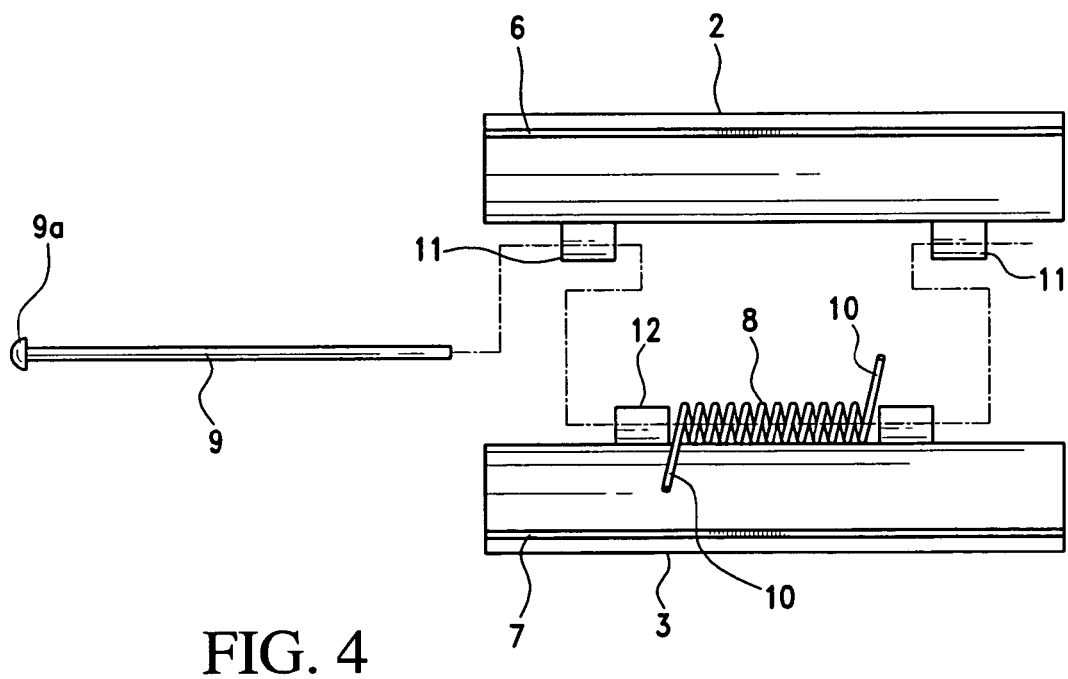
FIG. 4 shows an exploded rear view of a clip according to the current invention.

As shown in the rear view of FIG. 4 (sheath 4 omitted for clarity), the jaws are hinged together, where the jaws are articulated about an axle 9 passing through the hinge. Axle 9 passes through two outer brackets 11 mounted on upper jaw 2, and through two inner brackets 12 mounted on lower jaw 3. Axle 9 also passes through the center of helical spring 8. The axle 9 has a first end with a head 9a which is sufficiently to prevent it from passing through bracket 11, and a second end which passes through brackets 11 and 12. The axle is preferably made of a thermoplastic material. The axle, after passing through brackets 11 and 12, is secured in place by expanding the second end of the axle by heating it with a metal rod or similar device; after expansion, the second end of the axle is too large to pass through bracket 11.

Returning to FIGS. 2 and 3, sheath 4 is positioned between upper jaw 2 and lower jaw 4, with an upper surface of the sheath being secured to an inner surface of jaw 2 and a lower surface of the sheath being secured to an inner surface of jaw 3. When the jaws are closed, as in FIG. 2, longitudinal slit 5 in sheath 4 is likewise closed. Since sheath 4 is secured to both upper jaw 2 and lower jaw 4, opening the clip (FIG. 3) causes the sheath 4 to expand, opening longitudinal slit 5. Cords or tubes may then be inserted into sheath 4 through slit 5. When the clip is closed, slit 5 closes, retaining the cords or tubes within sheath 4. This prevents the cords or tubes from being caught within the jaws of the sheath. If desired, one side of slit 5 may be provided with ridges, and the other side of slit 5 may be provided with troughs. Upon closing the clip, the ridges will releasably snap into the troughs, helping to prevent the clip from accidentally opening.

The sheath may be made of an elastomeric material, such as styrene-butadiene rubber, polybutadiene, EPDM rubber, or natural rubber. Alternatively, the sheath may be made of a thermoplastic material. Such a thermoplastic material is preferably a plasticized polymer, such as polyolefin, polyester, nylon, or polyvinyl chloride. The sheath also may be made of a thermoplastic material, where the sheath has a living hinge opposite slit 5.

The sheath may be secured to the jaws in any number of ways. In one embodiment, the sheath is permanently secured to the jaws by means of an adhesive. In another embodiment, the sheath is removably secured to the jaws by means of Velcro, snaps, or the like.

Figure 5:
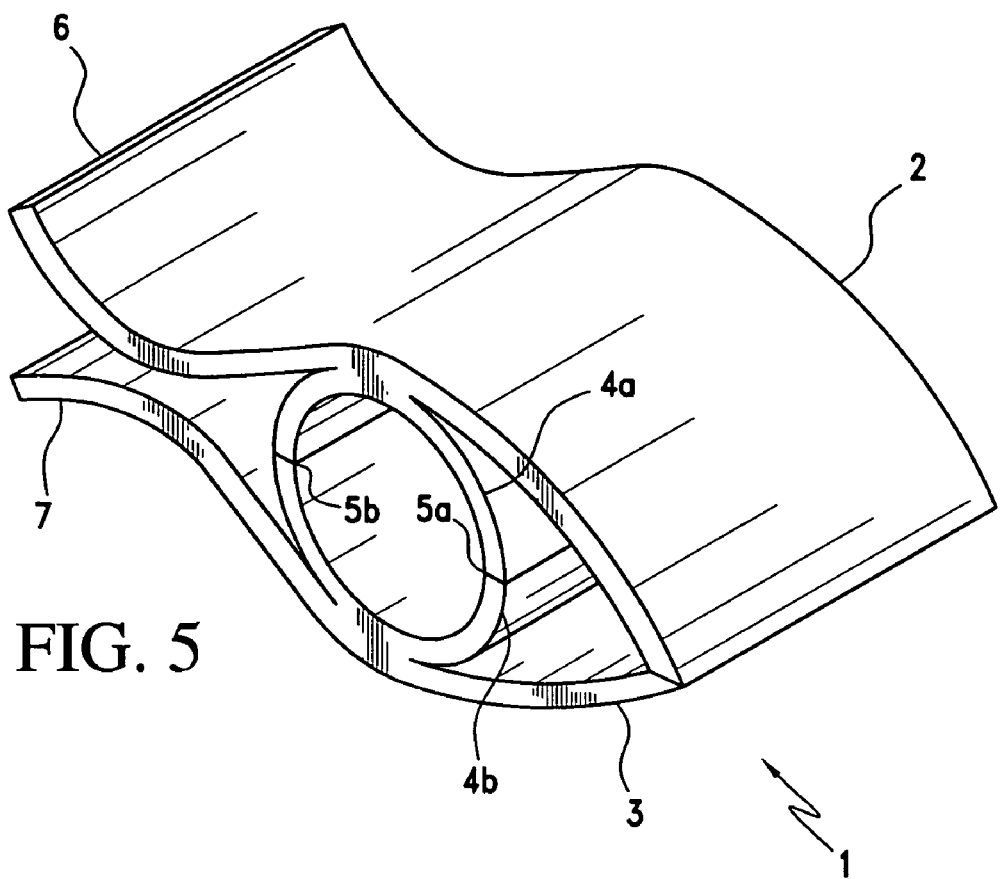
FIG. 5 shows a view of an alternate embodiment of a clip according to the current invention, in which the sheath is formed from two parts.
Figure 6:
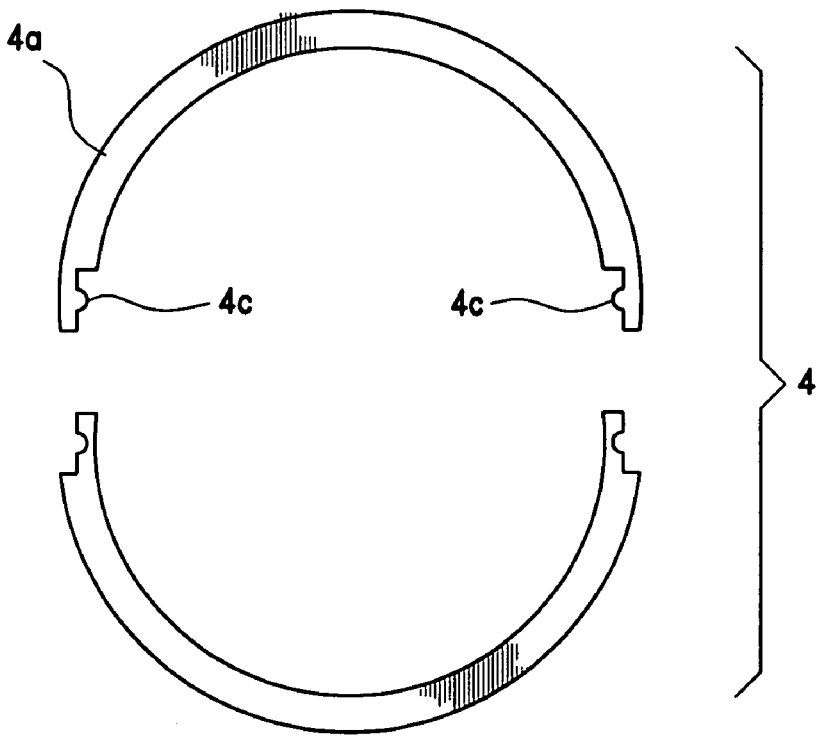
FIG. 6 shows a view of a sheath, in which the sheath is formed from two parts which snap together.

In a third embodiment (FIG. 5), the sheath is prepared in two parts by preparing jaw 2 with an upper part of the sheath 4a attached thereto, and preparing jaw 3 with a lower part of the sheath 4b attached thereto. For example, a jaw may be molded with a part of the sheath attached thereto. The sheath 4 is made of 4a and 4b, which meet so that sheath 4 has a first longitudinal opening 5a and a second longitudinal opening 5b on opposite sides of the sheath. The two-part sheath is connected between the jaws so that the longitudinal opening 5a is directed toward the point where the grasping parts of jaws 2 and 3 meet, while the longitudinal opening 5b is directed toward spring 8 (not shown in FIG. 5). Opening jaws 2 and 3 causes the sheath 4 to divide into an upper half 4a and a lower half 4b at the longitudinal openings 5a and 5b. If desired, upper half 4a may be provided with ridges 4c, and lower half 4b may be provided with troughs 4d (FIG. 6; jaws omitted for clarity). Upon closing the clip, ridges 4c will releasably snap into troughs 4d, helping to prevent the clip from accidentally opening.

In the embodiment of FIGS. 1-5, the jaws of the clip are shown as having straight edges. The clip having a straight edge may be used to secure cords or tubing to a wide variety of surfaces. For example, in a surgical environment, suction tubes and electrical cord for electrosurgical instruments may be positioned in sheath 4 while the clip is open, and then the clip may be closed about a surface to maintain the tubes and cords in a desired position where they may be conveniently accessed. The clip may thus be secured to a sheet or to a surgical tray. This also has the benefit of preventing the tubes from accidentally falling and contacting the floor or a nonsterile surface.

The clip may also be used in dentistry. For example, in a dentist's office, suction tubes are used by the dentist to remove saliva from the oral cavity. Electrical instruments having cords, particularly dental drills and electric toothbrushes, are used on the patient's teeth. To manage the tubes and cords, the suction tubes and electrical cords may be positioned in sheath 4 while the clip is open, and then the clip may be closed about a tray to maintain the tubes and cords in a desired position where they may be conveniently accessed.

Figure 7:
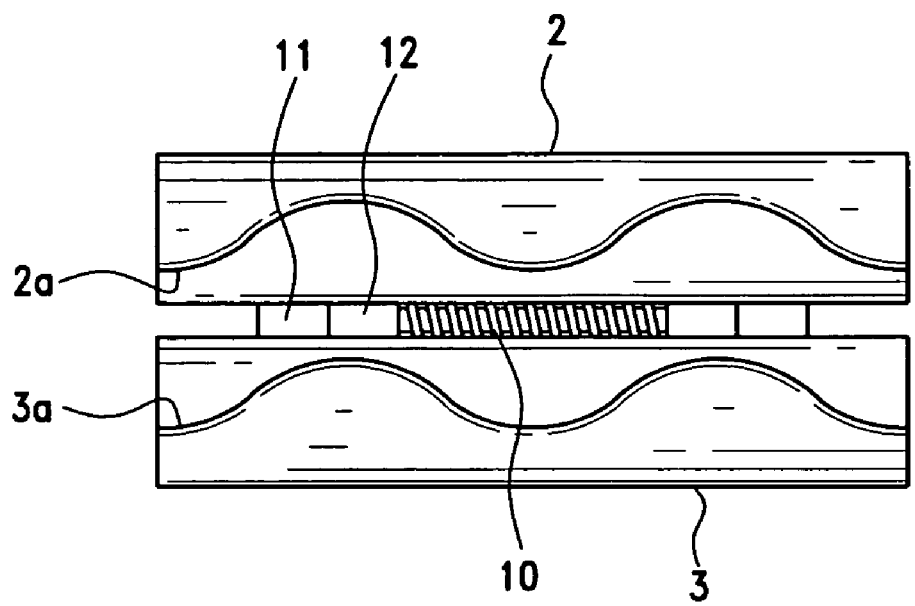
FIG. 7 shows an alternate embodiment of a clip according to the current invention, where the jaws of the clip have scalloped edges.
Figure 8:
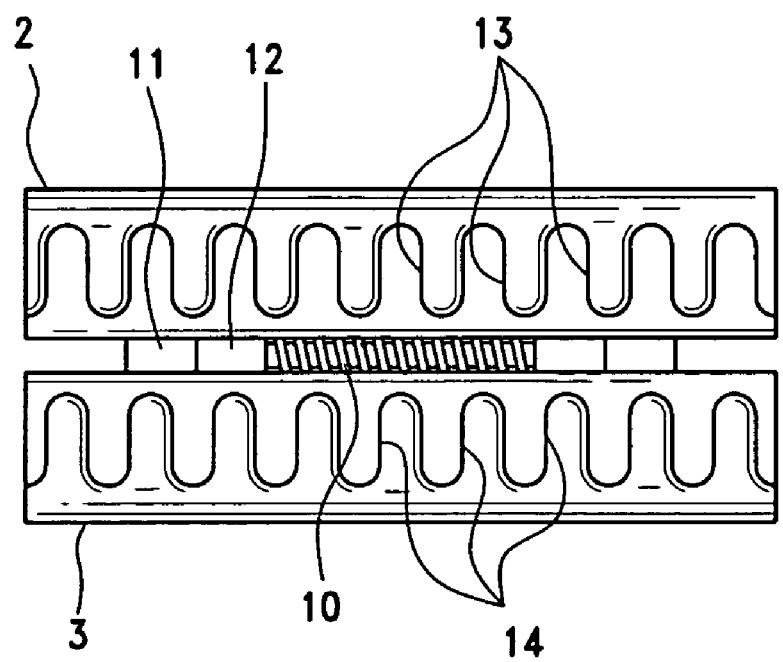
FIG. 8 shows an alternate embodiment of a clip according to the current invention, where the jaws of the clip have interlocking projections.

In another embodiment, the jaws of the clip may have curved or scalloped edges 2a and 3a (FIG. 7), where edges 2a and 3a have complementary curves. Where the straight-edged jaws are particularly suitable for attaching the clip to a rigid planar surface such as a tray, the scalloped jaws are ideally suited for a pre- or post-operative environment. For example, plastic or rubber drainage tubes are often used in post-operative patients to help remove blood and lymph which accumulates during the healing process. The tubes are normally attached to drainage bulbs, and may be pinned to a hospital gown. As a patient becomes mobile, it is not uncommon for drainage tubes to pull loose from hospital gowns, or to become entangled around objects. Intravenous (IV) tubing, during transport of patients in a wheelchair, or on a gurney, can also cause problems. Occasionally, the IV tubes may be entangled in the spokes or around the axle of the wheelchair or the gurney. The clip of FIG. 7 avoids this problem by allowing the clip to be attached to a textile surface. For example, after drainage tubes, IV tubes, or similar medical tubes are positioned within sheath 4, the clip may be attached to clothing or to bedding. Thus, for a bed-ridden patient, the clip may be attached to a sheet, pajamas, or a hospital gown. For a recovering patient who is regaining mobility, the clip may be secured to clothing. This greatly reduces the likelihood that drainage tubes or IV tubes will become entangled or accidentally pulled free of the patient's body. The advantage of the clip having scalloped jaws for this application is that the scalloped edges are less likely to slide along the fabric surface that the jaws of a clip having straight edges, reducing the likelihood that tubes clipped to sheets or clothing will accidentally pull free of the fabric. For additional security, a clip having jaws 2 and 3 with interlocking fingerlike projections 13 on upper jaw 2 and fingerlike projections 14 on lower jaw 3 may be used (FIG. 8). The fabric material may be interleaved between the projections 13 and 14 when the clip is closed, thereby making relative motion between the fabric and the clip difficult or impossible.

The clips described herein may also be used in various household applications. In particular, many household appliances, such as televisions, stereos, refrigerators, and lamps, have electrical cords which must be plugged into wall outlets. Sometimes, these appliances are not immediately adjacent to their wall outlets, and a length of electrical cord must be run across the floor. If the cord runs across major foot traffic areas, there is a risk that someone will be injured upon falling over the cord. The clip of the current invention is ideally suited to retain electrical cords within sheath 4. The clip may then be used to clip these electrical cords to cloth furniture coverings, to carpets, to curtains, or to tablecloths, so as to prevent electrical cords from entering foot traffic areas.

Although the present invention has been described in detail with particular reference to preferred embodiments thereof, it should be understood that the invention is capable of other different embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

Figure 9:
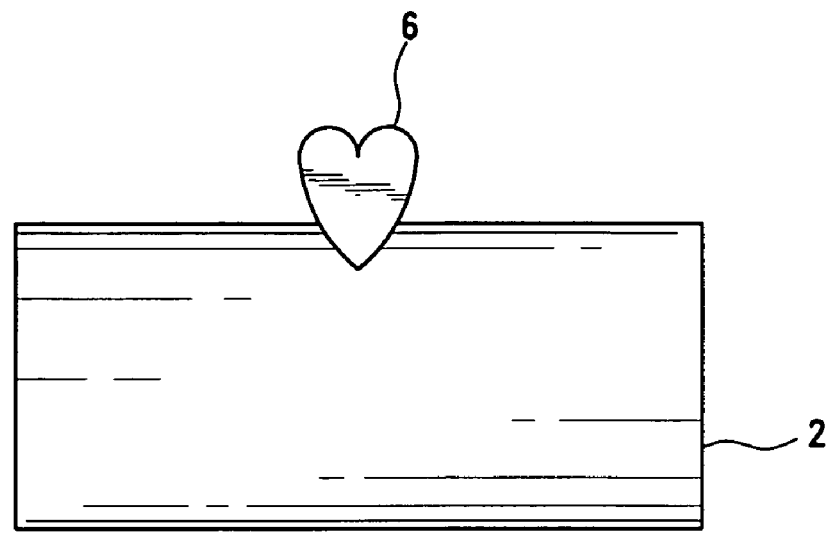
FIG. 9 shows a top view of an alternate embodiment of a clip according to the current invention, where a handle of the clip is molded in a decorative shape.

FIG. 9 shows an alternate embodiment of the clip in which the clip has a handle which is molded into a desired shape, rather than being generally rectangular, as shown in FIG. 1. For example, one or both of handles 6 and 7 may be molded in the shape of a heart, as shown in FIG. 1 (Only handle 6 is seen in FIG. 9.). Alternatively, they may be molded in the shape of footballs, baseballs, sports helmets, cartoon characters, or teddy bears, among other things. This is of particular utility in pediatric applications, as such shapes may be comforting to a frightened child who has undergone surgery.

Figure 10:
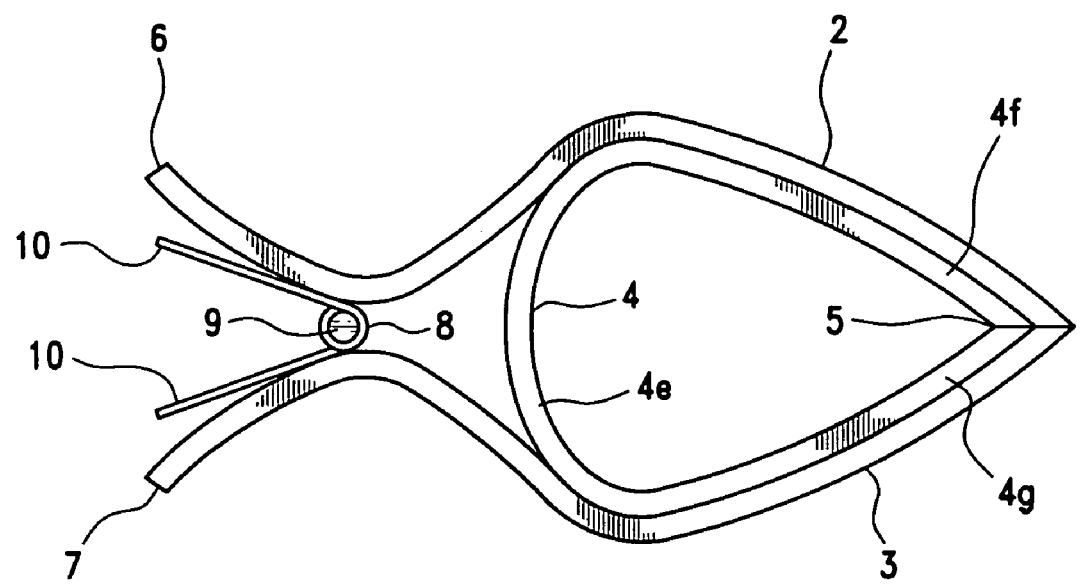
FIG. 10 shows a view of an alternate embodiment of a clip according to the current invention, in which the sheath conforms to the jaws.

FIG. 10 shows an alternate embodiment of clip 1 according to the current invention. Clip 1 features an upper jaw 2 and a lower jaw 3. Each jaw has a grasping edge. Jaws 2 and 3 are articulated about a hinge, allowing them to be moved between a closed position and an open position. Mounted in between jaws 2 and 3 is a sheath 4, with a longitudinal slit 5 running through the wall of the sheath. Sheath 4 is generally teardrop-shaped in cross section, with a rounded part 4e directed toward the hinge. A portion 4f of the sheath on one side of opening 5 generally conforms to shape of the grasping part of the upper jaw, and a portion 4g of the sheath on the other side of opening 5 generally conforms to the grasping part of the lower jaw. The longitudinal slit is directed toward the grasping edges of jaws 2 and 3. Upper jaw 2 has a handle 6 and lower jaw 3 has a handle 7.

Although the present invention has been described in detail with particular reference to preferred embodiments thereof, it should be understood that the invention is capable of other different embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

What is claimed is:

1. A clip for use in holding cords or tubing, comprising:
   an upper jaw and a lower jaw, each of them having a grasping part and articulated with respect to the other about a hinge between a closed position and an open position;
   a spring biasing said jaws into said closed position;
   a tubular sheath having at least one longitudinal opening, connected between said jaws, said at least one longitudinal opening being open when said jaws are in said open position and closed when said jaws are in said closed position; and
   a means for moving said jaws into said open position;
   wherein said sheath is adapted to receive cords or tubing through said at least one longitudinal opening when said jaws are in said open position, and retain said cords or tubing when said jaws are in said closed position; and
   wherein said jaws contact each other in said closed position.

2. A clip as in claim 1, wherein said sheath has a single longitudinal opening, and is connected between said jaws so that the longitudinal opening is directed toward said grasping parts by securing an upper surface of said sheath to said upper jaw and securing a lower surface of said sheath to said lower jaw.

3. A clip as in claim 1, wherein said sheath is permanently secured to said jaws.

4. A clip as in claim 1, wherein said sheath is permanently secured to said jaws by means of an adhesive.

5. A clip as in claim 1, wherein said sheath is made of a flexible plastic or an elastomer.

6. A clip as in claim 1, wherein said sheath is made of a thermoplastic having a hinge opposite said longitudinal opening.

7. A clip as in claim 6, wherein said hinge is a living hinge.

8. A clip as in claim 1, wherein said at least one longitudinal opening in said tubular sheath has two sides which snap together when said jaws are closed.

9. A clip as in claim 1, wherein said sheath has a first longitudinal opening and a second longitudinal opening on opposite sides of said sheath, and is connected between said jaws so that the first longitudinal opening is directed toward said grasping parts by securing an upper surface of said sheath to said upper jaw and securing a lower surface of said sheath to said lower jaw, wherein opening said jaws causes said sheath to divide into an upper half and a lower half at said first longitudinal opening and said second longitudinal opening.

10. A clip as in claim 9, wherein said upper half of said sheath is secured to said upper jaw, and said lower half of said sheath is secured to said lower jaw.

11. A clip as in claim 9, wherein said first longitudinal opening and said second longitudinal opening snap together when said jaws are closed.

12. A clip as in claim 11, wherein said upper half of said sheath and said upper jaw are molded as a single unit, and said lower half of said sheath and said lower jaw are molded as a single unit.

13. A clip as in claim 12, wherein said sheath is adapted to clip medical tubing or electrical cords to a surgical tray.

14. A clip as in claim 1, wherein said upper jaw and said lower jaw each have a substantially straight edge.

15. A clip as in claim 1, wherein said upper jaw and said lower jaw each have a curved edge, wherein the curved edge on the upper jaw interlocks with the curved edge on the lower jaw.

16. A clip as in claim 1, wherein said upper jaw and said lower jaw each have fingerlike projections, wherein the fingerlike projections on the upper jaw interlock with the fingerlike projections on the lower jaw.

17. A clip as in claim 1, wherein application of tension to the spring moves said jaws into the open position.

18. A clip as in claim 1, wherein said means for moving said jaws includes a handle connected to said upper jaw and a handle connected to said lower jaw, said spring being connected between said handles.

19. A clip as in claim 18, wherein said handles are molded in the shape of hearts, footballs, baseballs, sports helmets, cartoon characters, or teddy bears.

20. A clip as in claim 1, wherein said sheath is adapted to retain medical tubing.

21. A clip as in claim 1, wherein said sheath is adapted to retain medical IV tubing or medical drainage tubes.

22. A clip as in claim 1, wherein said sheath is adapted to clip medical tubing to a sheet or to clothing.

23. A clip as in claim 1, wherein said sheath is adapted to retain electrical cords.

24. A clip as in claim 1, wherein said sheath is adapted to clip electrical cords to cloth furniture coverings, to carpets, to curtains, or to tablecloths.

25. A clip as in claim 1, wherein said tubular sheath has a circular cross section.

26. A clip for use in holding cords or tubing, comprising:
an upper jaw and a lower jaw, each of them having a grasping part and articulated with respect to the other about a hinge between a closed position and an open position;
a spring biasing said jaws into said closed position;
a sheath having at least one longitudinal opening, connected between said jaws, wherein one side of said opening conforms to the grasping part of the upper jaw and the other side of said opening conforms to the grasping part of the lower jaw; and
a means for moving said jaws into said open position;
wherein said sheath is adapted to receive cords or tubing through said at least one longitudinal opening when said jaws are in said open position; and
wherein said jaws contact each other in said closed position.

27. A clip for use in holding cords or tubing, comprising:
an upper jaw and a lower jaw, each of them having a grasping part and articulated with respect to the other about a hinge between a closed position and an open position;
a spring biasing said jaws into said closed position;
a tubular sheath having at least one longitudinal opening, connected between said jaws, said at least one longitudinal opening being open when said jaws are in said open position and closed when said jaws are in said closed position; and
a means for moving said jaws into said open position;
wherein said sheath is adapted to receive cords or tubing through said at least one longitudinal opening when said jaws are in said open position, and retain said cords or tubing when said jaws are in said closed position, and
wherein said sheath is removably secured to said jaws.

* * * * *